United States Patent
Imbimbo et al.

(10) Patent No.: US 9,150,489 B2
(45) Date of Patent: Oct. 6, 2015

(54) 1-(2-FLUOROBIPHENYL-4-YL)-ALKYL CARBOXYLIC ACID DERIVATIVES FOR THE THERAPY OF TRANSTHYRETIN AMYLOIDOSIS

(75) Inventors: Bruno Pietro Imbimbo, Parma (IT); Gino Villetti, Parma (IT); Rodolfo Berni, Parma (IT)

(73) Assignee: CHIESI FARMACEUTICI S.p.A., Parma (IT)

( * ) Notice: Subject to any disclaimer, the term of this patent is extended or adjusted under 35 U.S.C. 154(b) by 549 days.

(21) Appl. No.: 13/091,195

(22) Filed: Apr. 21, 2011

(65) Prior Publication Data

US 2011/0263711 A1 Oct. 27, 2011

(30) Foreign Application Priority Data

Apr. 21, 2010 (EP) ..................................... 10160564

(51) Int. Cl.
*C07C 57/58* (2006.01)
*A61K 31/192* (2006.01)

(52) U.S. Cl.
CPC ................ *C07C 57/58* (2013.01); *A61K 31/192* (2013.01)

(58) Field of Classification Search
CPC .............................. C07C 57/58; A61K 31/192
USPC .......................................... 514/568; 562/493
See application file for complete search history.

(56) References Cited

U.S. PATENT DOCUMENTS

2005/0288375 A1 * 12/2005 Hobden et al. ............... 514/569

FOREIGN PATENT DOCUMENTS

| EP | 2 133 322 | 12/2009 |
|---|---|---|
| WO | 2004/056315 | 7/2004 |
| WO | WO 2004074232 A1 * | 9/2004 |
| WO | 2006/020850 | 2/2006 |
| WO | 2009/040405 | 4/2009 |

OTHER PUBLICATIONS

Suhr et. al., Journal of Internal Medicine, 2003, Blackwell Publishing, vol. 254, pp. 225-235.*
Cole et. al., Journal of Medicinal Chemistry, 2003, American Chemical Society, vol. 46, pp. 207-209.*
Zhu et. al., Bioorganic and Medicinal Chemistry Letters, 2000, Pergamon, vol. 10, pp. 1121-1124.*
Sousa et. al., Progress in Neurobiology, 2003, Elsevier, vol. 71, pp. 385-400.*
U.S. Appl. No. 13/723,662, filed Dec. 21, 2012, Imbimbo.
U.S. Appl. No. 13/078,039, filed Apr. 1, 2011, Pivetti, et al.
European Search Report in Application No. 10160564.0, issued Jan. 31, 2011.
Peretto I. et al., J. Med. Chem. (2005), vol. 48, No. 18, pp. 5705-5720.
Imbimbo, B.P. et al., British Journal of Pharmacology (2009), vol. 156, pp. 982-993.
S.C. Shin, et al., Mt. Sinai J. Med., vol. 79 (6), pp. 733-748 (2012).
A.P. Barreiros, et al., Dig. Dis., vol. 31, pp. 170-174 (2013).

* cited by examiner

*Primary Examiner* — Sarah Pihonak
(74) *Attorney, Agent, or Firm* — Oblon, McClelland, Maier & Neustadt, L.L.P.

(57) ABSTRACT

Derivatives of 1-(2-fluorobiphenyl-4-yl)-alkyl carboxylic acid are capable of stabilizing the tetrameric native state of transthyretin for the prophylaxis and treatment of amyloidosis.

25 Claims, No Drawings

1-(2-FLUOROBIPHENYL-4-YL)-ALKYL CARBOXYLIC ACID DERIVATIVES FOR THE THERAPY OF TRANSTHYRETIN AMYLOIDOSIS

CROSS REFERENCES TO RELATED APPLICATIONS

This application claims priority to European Patent Application No. 10160564.0 filed on Apr. 21, 2010, which is incorporated herein by reference in its entirety.

BACKGROUND OF THE INVENTION

1. Field of the Invention

The present invention relates to therapies of amyloidosis. More particularly, the present invention relates to the use of 1-(2-fluorobiphenyl-4-yl)-alkyl carboxylic acid derivatives as agents capable of stabilizing the tetrameric native state of transthyretin for the prophylaxis and treatment of amyloidosis.

2. Discussion of the Background

Amyloidosis is a serious disease caused by extracellular deposition of insoluble abnormal fibrils. Systemic amyloidosis, with deposits in the viscera, blood vessels, and connective tissue, is usually fatal, causing about one per thousand deaths in developed countries.

Amyloid is deposited when there is: (i) sustained exposure to either normal or increased concentrations of a normal, potentially amyloidogenic, protein; (ii) when an abnormal amyloidogenic protein is produced as a consequence of an acquired disease; or (iii) when a gene mutation encodes an amyloidogenic variant protein. Fibrillogenesis results from reduced stability of the native fold of the fibril precursor protein, so that under physiological conditions it populates partly unfolded intermediate states which aggregate as stable amyloid fibrils.

Wild type-transthyretin (WT-TTR) is the normal plasma protein, synthesized by hepatocytes and by the choroid plexus, which transports thyroid hormone and retinol binding protein. TTR is inherently amyloidogenic and forms microscopic amyloid deposits of uncertain clinical significance in all individuals aged over 80 years. Massive deposits in the heart can also occur, causing fatal senile systemic amyloidosis (SSA). The inherent amyloidogenicity of wild type transthyretin is markedly enhanced by most of the reported >80 different point mutations which encode single residue substitutions in the transthyretin sequence. These mutations cause autosomal dominant adult onset hereditary amyloidosis, a universally fatal condition affecting about 10,000 patients worldwide. Said diseases are mainly grouped into two broad groups: familial amyloid polyneuropathy (FAP) and familial amyloid cardiomiopathy (FAC).

Amyloidogenic mutations occur in all ethnic groups, but by far the most common, V30M, clusters in three geographical foci: Northern Portugal, Northern Sweden, and parts of Japan. Other common amyloidogenic variants are T60A, L58H, L55P, I84S, and V112I. Among the pathogenic variants of TTR so far identified, the V122I variant is of particular importance as is carried by 3-4% of African Americans: 1.3 million people, including 13,000 individuals homozygous for the mutation. It is the second most common pathogenic mutation in that population after sickle cell haemoglobin.

The variant V122I is particularly associated to cardiac transthyretin amyloidosis which presents as progressive, ultimately fatal, heart failure due to restrictive cardiomyopathy. Said pathology is rarely suspected and is usually misdiagnosed as coronary heart disease.

So far there is only a treatment available for FAP, i.e. gene therapy mediated by surgical replacement of the patient's liver, the organ secreting TTR subject to misfolding into the blood stream. The disadvantages of this approach include its invasiveness for the donor and recipient, the requirement for life-long immune suppression, and the limited effectiveness for some mutations for reasons that are not yet clear. Currently, there is no effective treatment either for SSA associated with WT-TTR deposition or for FAC. Therefore, a small molecule therapeutic strategy for all TTR-based amyloid diseases would be highly advantageous.

The most common approach to the potential treatment of transthyretin amyloidosis has been to identify small molecule ligands able to stabilize the native TTR tetrameric structure and thereby to prevent the dissociation of TTR into monomers which are in turn prone to misassembly leading to fibrillogenic aggregation. Ideally, good fibrillogenesis inhibitors should bind with high affinity, dissociate slowly, and exhibit high binding selectivity to TTR in the blood.

For example, several non-steroidal anti-inflammatory drugs (NSAIDS) such as diclofenac, flufenamic acid, diclofenac, flurbiprofen, and diflunisal have been shown to act as stabilizers of the tetrameric structure of TTR, inhibiting the formation of TTR amyloid fibrils in vitro. However, because said drugs are cyclooxygenase-2 inhibitors, their long-term administration could lead to gastrointestinal side effects.

Polyphenols such as trans-resveratrol are known to bind specifically to thyroxine binding sites of TTR (see Klabunde et al., Nat. Struct. Biol., 2000, 7, 312). However said kind of drugs are also known to be very aspecific, they might have low bioavailability, and may be endowed with several ancillary effects.

Further derivatives enabling for TTR binding are described in WO 2004/056315, WO 2006/086517, WO 2007022138, and WO 2009/040405.

In view of the above considerations, there is still the need for more effective products with an established safety profile in humans that binds to TTR and hence can be useful for treating TTR amyloidosis.

WO 2004/074232 and WO 2004/073705 disclose therapeutic agents for neurodegenerative diseases such as Alzheimer's disease.

SUMMARY OF THE INVENTION

Accordingly, it is one object of the present invention to provide novel methods for the prevention and/or treatment of transthyretin (TTR) amyloidosis diseases.

This and other objects, which will become apparent during the following detailed description, have been achieved by the inventors' discovery that compounds of general formula (I)

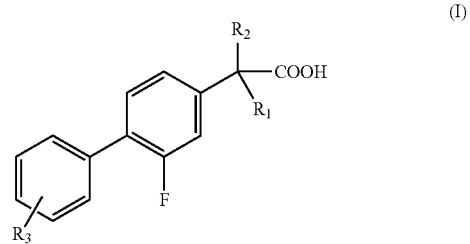

wherein

R₁ is hydrogen or linear or branched $C_1$-$C_4$ alkyl, preferably methyl;

R₂ is linear or branched $C_1$-$C_4$ alkyl, preferably methyl, or R₁ and R₂ taken together with the carbon atom to which they are linked form a 3 to 6 carbon atoms ring, preferably cyclopropyl; and R₃ represents one or more groups, which are the same or different from each other, independently selected from halogen atoms, preferably chlorine;

are useful for the prevention and/or treatment of transthyretin (TTR) amyloidosis diseases.

In a second aspect, the present invention provides the use of the compounds of general formula (I) in the manufacture of a medicament for the prevention and/or treatment of transthyretin (TTR) amyloidosis diseases.

In another aspect, the present invention provides the above uses of polymorphs, pharmaceutically acceptable salts and pro-drugs of the compounds of general formula (I).

In a further aspect, the present invention provides a method for preventing and/or treating systemic amyloidosis in a patient, comprising administering to said patient an effective amount of a compound of general formula (I), including polymorphs, pharmaceutically acceptable salts and pro-drugs thereof It has now been found that certain halogen derivatives therein described can effectively be used for preventing and/or treating TTR amylioidosis.

DETAILED DESCRIPTION OF THE PREFERRED EMBODIMENTS

Unless otherwise provided in the present description, within the compounds of general formula (I), the phenyl ring bears one or more halogen atoms therein referred to as R₃ groups.

From the above, it is clear to the skilled person that any of the said halogen atoms, which can be the same or different from each other, may be thus present in any possible free position of the phenyl ring itself.

The term "halogen atoms" includes fluorine, chlorine, bromine, and iodine.

The expression "linear or branched $C_1$-$C_4$ alkyl" refers to straight-chained and branched-chained alkyl groups wherein the number of constituent carbon atoms is in the range 1 to 4. Exemplary alkyl groups are methyl, ethyl, n-propyl, isopropyl, and tert-butyl.

The expression "3 to 6 carbon atoms ring" refers to cyclic non-aromatic hydrocarbon groups containing from 3 to 6 carbon atoms. Examples include cyclopropyl, cyclobutyl, cyclopentyl, and cyclohexyl.

The term "polymorphs" refers to a different crystal structure of the same solid substance. They exhibit different melting points, solubilities (which affect the dissolution rate of the drug and consequently its bioavailability in the body), X-ray crystal and diffraction patterns.

The expression "substantially pure polymorph" refers to a sample in which the polymorph is present in a substantial excess over other polymorphs of the same compound, i.e. in an amount exceeding 75%, more preferably exceeding 90%, even more preferably exceeding 95%, and most preferably exceeding 99% by weight of the total weight of the compound in the sample.

The term "prodrug" refers to a substance administered in an inactive form that is then metabolized in the body in vivo into the active compound with the aim of optimizing absorption, distribution, metabolism, and excretion.

The term "TTR amyloidosis" refers to a form of amyloidosis disease due to the misfolding of the transthyretin protein.

The term "prophylaxis" refers to the use for reducing the occurrence of the disease, while the term "treatment" refers to the use for palliative, curing, symptom-allievating, symptom-reducing, disease regression-inducing therapy.

Transthyretin (TTR) is a 55 kDa homotetramer characterized by 2,2,2 symmetry, having two identical funnel-shaped binding sites at the dimer-dimer interface, where the thyroid hormone L-thyroxine (T4) can be bound in blood plasma and cerebrospinal fluid. Besides taking part in the transport of T4, TTR forms a macromolecular complex with the retinol binding protein, thereby participating also in the transport of retinol. The binding sites of thyroxine and retinol-binding protein are present in distinct regions of TTR, such that there is no interdependence of the binding of the hormone and of retinol-binding protein.

TTR misfolding including tetramer dissociation render the protein capable of misassembly, ultimately affording amyloid aggregates. Misfolding of transthyretin (TTR), including tetramer dissociation into monomers followed by tertiary structural changes within the monomer, is sufficient for TTR misassembly into amyloid and other abnormal quaternary structures associated with three TTR amyloidosis diseases: senile systemic amyloidosis (SSA), familial amyloid polyneuropathy (FAP), and familial amyloid cardiomyopathy (FAC).

The present invention is thus directed to the compounds of general formula (I)

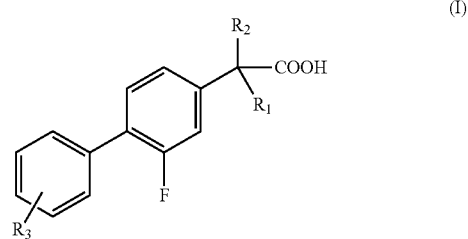

(I)

wherein R₁, R₂ and R₃ have the above reported meanings, including polymorphs, pharmaceutically acceptable salts and pro-drugs thereof, for use in the prevention and/or treatment of transthyretin (TTR) amyloidosis diseases.

Likewise, as per the following details, the present invention also relates to the use of the above compounds and derivatives thereof, in the manufacture of a medicament for the prophylaxis and/or treatment of TTR amyloidosis diseases.

The present invention is based, at least in part, on the discovery that compounds of formula (I) have the effect of stabilizing the TTR tetramer and are hence excellent inhibitors of TTR tetramer dissociation and TTR amyloidogenesis.

In particular, some representative members of said class of compounds have a higher binding affinity to TTR as compared to trans-resveratrol, whereas the latter compound exhibits a higher binding affinity as compared to diflunisal and 2-(3, 5-dichlorophenyl)-1, 3-benzoxazole-6-carboxylic acid, also known as tafamidis, the most representative compound of WO 2009/040405. This may in turn provide for a better stabilization of the non-amyloidogenetic tetrameric form of TTR.

A first group of preferred compounds of general formula (I) is that wherein the phenyl ring bearing one or more substituents $R_3$ is substituted in 3' and 5' positions with two chlorine atoms, according to the general formula (II) below

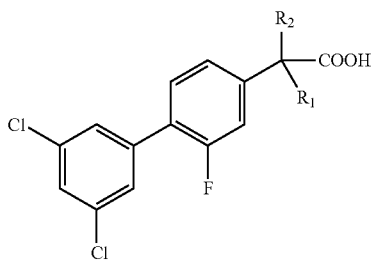

wherein $R_1$ and $R_2$ are as defined above.

In preferred embodiments, $R_1$ is H and $R_2$ is methyl or, alternatively, both $R_1$ and $R_2$ are methyl.

In another preferred embodiment, $R_1$ and $R_2$ together with the carbon atom to which they are linked form a cyclopropyl group.

Preferred compounds of formula (II) are the following:
2-(3',5'-dichloro-2-fluoro-biphenyl-4-yl) propionic acid;
2- methyl-(3',5'-dichloro-2-fluoro-biphenyl-4-yl) propionic acid (herein referred to with the experimental code CHF 4795); and
(3',5'-dichloro-2-fluorobiphenyl-4-yl)cyclopropanecarboxylic acid.

A second group of preferred compounds of general formula (I) is that wherein the phenyl ring bearing one or more $R_3$ substituents is substituted in 3' and 4' positions with two chlorine atoms, according to the general formula (III)

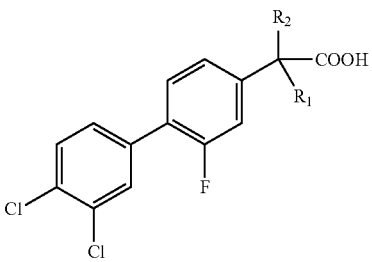

In a preferred embodiment, $R_1$ is H and $R_2$ is methyl or, alternatively, both $R_1$ and $R_2$ are methyl.

In another preferred embodiment, $R_1$ and $R_2$ together with the carbon atom to which they are linked form a cyclopropyl group.

Preferred compounds of formula (III) are the following:
2-(3',4'-dichloro-2-fluoro-biphenyl-4-yl) propionic acid;
2-methyl-(3',4'-dichloro-2-fluoro-biphenyl-4-yl) propionic acid; and
1-(3',4'-dichloro-2-fluorobiphenyl-4-yl)cyclopropanecarboxylic acid (herein also referred to with the experimental code CHF 5074).

CHF 5074 is a particularly preferred compound.

The compounds of general formula (I) may advantageously be used in any form, either amorphous or crystalline, including solvates or hydrates thereof. Preferably, they are used in crystalline form.

For example, as disclosed in the co-pending European Patent Application No. EP 10158954.7 (corresponds to U.S. patent application Ser. No. 13/078,039, filed April 1, 2011), the entire content of which is incorporated herein by reference, CHF 5074 can exist in three stable crystalline polymorphic forms. Accordingly, the present invention includes the use of any of said polymorphs, either in substantially pure form or admixed in any proportion.

In view of the close relationship between the compounds of general formula (I) in free acid form and those in the form of salts, the present invention is also directed to the use of pharmaceutically acceptable salts thereof.

Pharmaceutically acceptable salts according to the invention thus include those formed with both common organic and inorganic bases. For example, the salts disclosed in the co-pending patent European Patent Application No. EP 10158954.7, may advantageously be utilized.

The compounds of general formula (I) may also be administered in form of prodrugs. Suitable prodrugs may be esters with common alcohols for pharmaceutical use such as ethanol or polyalcohols such as sorbitol, with sugars such as glucose, or with sugar acids such as ascorbic acid. Other suitable prodrugs may be those disclosed in WO 2006/016219, which is incorporated herein by reference in its entirety.

The compounds of formula (I) and the salts and prodrugs thereof may be synthesized as described in U.S. patent application Ser. Nos. 12/466,660, filed May 15, 2009, and 12/846,341, filed Jul. 29, 2010, both of which are incorporated herein by reference in their entireties.

The compounds of general formula (I) may be combined with one or more pharmaceutically acceptable carriers or excipients to provide suitable pharmaceutical compositions. The pharmaceutically acceptable carriers or excipients may be advantageously selected from the group consisting of, diluents, wetting agents, emulsifying agents, binders, coatings, fillers, glidants, lubricants, disintegrants, preservatives, stabilizers, surfactants, pH buffering substances, flavouring agents and the like. Comprehensive guidance on pharmaceutical excipients is given in Remington's Pharmaceutical Sciences Handbook, XVII Ed. Mack Pub., N.Y., U.S.A, which is incorporated herein by reference.

The pharmaceutical compositions of the invention may be formulated for administration by any convenient route, e.g. by oral, parenteral, topical, inhalation, buccal, nasal, rectal, vaginal, transdermal administration. Suitable dosage forms can include tablets, capsules, lozenges, suppositories, solutions, emulsions, suspensions, syrups, ointments, creams, oils, and powders. Preferably, the pharmaceutical compositions of the invention will be administered orally using appropriate dosage forms, such as capsules, tablets, caplets etc.

The dosage of the compounds of general formula (I) and of their salts and prodrugs can vary within wide limits depending on the nature of the disease to be treated, the type of patient, and the mode of administration. A person skilled in the art can determine a therapeutically effective amount for each patient and thereby define the appropriate dosage. For example, when the compound quoted with the code CHF 5074 is administered by oral route to humans, a typical daily dosage might fall within the range of 5 to 2000 mg, preferably between 100 mg and 1000 mg, administered in a single or multiple daily dosage units. Thus, a single dose of the pharmaceutical preparations of the invention conveniently comprises between about 100 and 1000 mg of CHF 5074 or salt thereof.

The compounds of the present invention may be of use in the treatment or prophylaxis of any wild type TTR amyloidosis disease. They may be also of use for delaying the onset or slowing the progression of said diseases.

In a preferred mode, the wild-type TTR amyloidosis disease is senile systemic amyloidosis, or familial amyloidosis polyneuropathy. More particularly, the familial amyloidosis polyneuropathy (FAP) is characterized by V30M mutation. In another preferred mode, the transthyretin amyloidosis disease is familial amyloidosis cardiomyopathy (FAC). More particularly, the familial amyloidosis cardiomyopathy is characterized by a V122I mutation.

Other features of the invention will become apparent in the course of the following descriptions of exemplary embodiments which are given for illustration of the invention and are not intended to be limiting thereof.

EXAMPLES

Example 1

Analysis of the Interaction With Wild-Type Human Transthyretin (TTR), By Using Fluorometric Techniques The aim of this study is to investigate whether representative compounds of the invention are able to stabilize the oligomeric native state of TTR through the interaction with the thyroxine binding sites in comparison to reference compounds. Recombinant human wild-type TTR and some of its major amyloidogenic genetic variants were produced using *E. coli* as expression organism as reported in Zanotti et al., *FEBS J.*, 2008, 275, 5841, which is incorporated herein by reference.

To compare binding properties of the compounds CHF 5074 and CHF 4795 with those of trans-resveratrol, diflunisal and tafamidis, the interactions of such compounds with wild-type TTR were analyzed. The analysis of interactions was based on fluorescence measurements. It is known that the fluorescence emission of the two fluorescent probes 8-anilino-1-naphthalene sulfonate (ANS) and trans-resveratrol increases substantially when these compounds are specifically bound within thyroxine binding sites in TTR (see Smith et al., *Biochim. Biophys. Acta,* 1994, 1199, 76, and Reixach et al., *J. Biol. Chem.,* 2008, 283:2098, respectively, both or which are incorporated herein by reference).

While ANS possesses a relatively low binding affinity for TTR, trans-resveratrol has a high binding affinity, greater than that of thyroxine. In competitive binding experiments, using the fluorescence signals provided by the two fluorescent probes, or by those of the comparative compounds, we were able to assess the relative affinity of CHF 5074, CHF 4795, trans-resveratrol, diflunisal and tafamidis for human TTR. All data were obtained at 20° C. in the presence of 50 mM Na phosphate buffer, pH 7.2, 150 mM NaCl.

The results were the following:

The fluorescence emission (excitation at 320 nm) of unbound trans-resveratrol (10 µM) was quite low and increased substantially upon binding to TTR (5 µM). The emission peak of TTR-bound trans-resveratrol (maximum at approx. 390 nm) was nearly completely abolished in the presence of 10 µM CHF 5074 or CHF 4795, consistent with a higher binding affinity of said compounds relative to that of trans-resveratrol.

The fluorescence emission (excitation at 360 nm) of unbound ANS (10 µM) was quite low and increased substantially upon binding to TTR (5 µM).

The emission peak of TTR-bound ANS was nearly completely abolished in the presence of 10 µM CHF 5074 or CHF 4795, consistent with a higher binding affinity of said compounds relative to that of ANS.

The fluorescence emission (excitation at 320 nm) of unbound tafamidis (10 µM) was characterized by a maximum at approximately 375 nm, whereas in the presence of 10 µM TTR its emission was significantly enhanced and was red shifted by approximately 40 nm. The emission peak of TTR-bound tafamidis (10 µM) was nearly completely shifted to that of unbound tafamidis in the presence of 10 µM CHF 5074 or CHF 4795, consistent with a higher binding affinity of CHF 5074 and CHF 4795 relative to that of tafamidis. The fluorescence emission of 10 µM TTR-bound tafamidis (maximum at approximately 415 nm) was nearly completely shifted to that of TTR-bound trans-resveratrol and unbound tafamidis (maximum at approximately 380 nm) upon incubation of TTR-bound tafamidis with 10 µM resveratrol, consistent with a higher binding affinity of trans-resveratrol relative to that of tafamidis.

The fluorescence emission upon excitation at 320 nm of bound and unbound diflunisal (10 µM) was characterized by similar intensities and maxima (at approximately 420 nm); the intensity of fluorescence emission of TTR-bound diflunisal was drastically reduced upon excitation at 340 nm. Under the latter excitation condition, when TTR-bound diflunisal (10 µM) was exposed to equimolar trans-resveratrol, a spectrum similar to that of TTR-bound trans-resveratrol rather than to that of TTR-bound diflunisal was obtained, consistent with a higher binding affinity of trans-resveratrol relative to that of diflunisal.

Taken together, the data of competitive binding assays have shown that CHF 5074 and CHF 4795 have a higher binding affinity to TTR as compared to trans-resveratrol, whereas the latter compound exhibits a higher binding affinity as compared to tafamidis and diflunisal.

The quite high affinity exhibited by CHF 5074 and CHF 4795 appears to be very advantageous for two reasons: i) since TTR stabilization is due to the binding of ligands inside the thyroxine binding sites, a larger stabilizing effect is expected for ligands with the highest affinity, at least at the neutral pH (close to that of blood plasma) used in competitive binding experiments; and ii) a higher binding selectivity for TTR is expected for high affinity ligands in blood plasma, where other binding proteins, especially serum albumin, might compete with TTR for the binding of inhibitors of TTR fibrillogenesis.

Example 2

Evaluation of the Inhibitory Effect on In Vitro Fibrillogenesis By Human Wild-Type TTR and Two Major Amyloidogenic Variants (V30M and V 122I)

The aim of this study was to evaluate the inhibitory effect of the same representative compounds of the inventions tested in Example 1 in vitro fibrillogenesis by human wild-type TTR and two major amyloidogenic variants (V30M and V 122I) at moderately acidic pH, in comparison to reference compounds. To highlight the inhibitory effect of CHF 5074 and CHF 4795 versus diflunisal and tafamidis on in vitro fibrillogenesis by wild-type, V30M and V122I TTR at moderately acid pH, we followed the kinetics of fibril formation by these proteins, by monitoring the increase in turbidity at 400 nm as reported in Johnson et al., 2008, *J. Med. Chem.,* 51:260 (which is incorporated herein by reference), upon incubation with TTR. The final concentration of TTR was of 3.6 µM, which is close to its physiological plasma concentration, with fibrillogenesis inhibitors at a final concentration of 10.8 µM. According to the procedure adopted for other inhibitors of fibrillogenesis (Johnson et al., 2008, J. Med. Chem., 51:260), TTR was incubated with each inhibitor at neutral pH (10 mM Na phosphate buffer, pH 7.2, 100 mM KCl, 1 mM EDTA) for 30 minutes at ambient temperature, prior to the incubation of the protein at acidic pH (200 mM Na Acetate buffer, pH 4.4, 100 mM KCl, 1 mM EDTA) at 37° C. in order to promote fibrillogenesis. Inhibitory effect data represent the average of two independent measurements for each compound.

The results are the following.

The kinetics of wild-type TTR fibrillogenesis is nearly complete within 100 hours upon incubation at acidic pH. CHF 5074, CHF 4795 and the reference compounds diflunisal and tafamidis exhibited quite similar inhibitory effects (about 75% inhibition) on fibrillogenesis.

The kinetics of V30M TTR fibrillogenesis was similar to that obtained with wild-type TTR. CHF 5074, CHF 4795, and the reference compounds diflunisal and tafamidis exhibited inhibitory effects similar to those observed with wild-type TTR.

The kinetics of V122I TTR fibrillogenesis appeared to be remarkably faster as compared to wild-type TTR in the same conditions, and at the same time CHF 5074, CHF 4795, and the reference compounds diflunisal and tafamidis exhibited more pronounced inhibitory effects (about 92% inhibition) on fibrillogenesis.

Taken together, the data demonstrate a remarkable inhibitory effect on TTR fibrillogenesis for CHF 5074 and CHF 4795, similar to that of reference compounds that are currently studied for therapeutic use in TTR amyloidoses.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A method for alleviating or reducing the symptoms of, or providing palliative care of, or providing regression of a transthyretin (TTR) amyloidosis disease selected from the group consisting of senile systemic amyloidosis, familial amyloidosis polyneuropathy, and familial amyloidosis cardiomyopathy, comprising administering, to a subject in need thereof, a compound of formula (I):

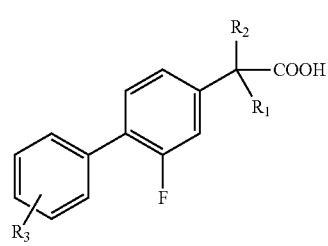

wherein
$R_1$ and $R_2$ are both methyl;
or $R_1$ and $R_2$ taken together with the carbon atom to which they are linked, form a cyclopropyl group; and
$R_3$ represents one or more chlorine atoms;
or a pharmaceutically acceptable salt thereof.

2. A method according to claim 1, wherein said disease is familial amyloidosis cardiomyopathy.

3. A method according to claim 2, wherein said familial amyloidosis cardiomyopathy is characterized by a V122I mutation.

4. A method according to claim 1, which comprises administering a compound of formula (II)

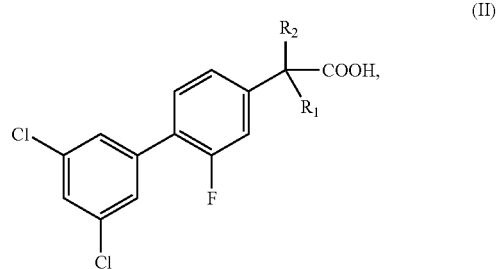

or a pharmaceutically acceptable salt thereof.

5. A method according to claim 4, wherein both $R_1$ and $R_2$ are methyl.

6. A method according to claim 4, wherein $R_1$ and $R_2$ together with the carbon atom to which they are linked form a cyclopropyl group.

7. A method according to claim 4, which comprises administering a member selected from the group consisting of
2- methyl-(3',5'-dichloro-2-fluoro-biphenyl-4-yl)propionic acid;
a pharmaceutically acceptable salt of 2- methyl-(3',5'-dichloro-2-fluoro-biphenyl-4-yl)propionic acid;
(3',5'-dichloro-2-fluorobiphenyl-4-yl)cyclopropanecarboxylic acid; and
a pharmaceutically acceptable salt of (3',5'-dichloro-2-fluorobiphenyl-4-yl)cyclopropanecarboxylic acid.

8. A method according to claim 1, which comprises administering a compound of formula (III):

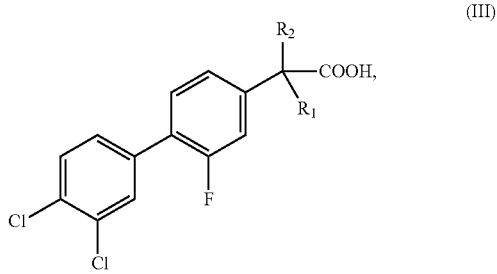

or a pharmaceutically acceptable salt thereof.

9. A method according to claim 8, wherein both $R_1$ and $R_2$ are methyl.

10. A method according to claim 8, wherein $R_1$ and $R_2$ together with the carbon atom to which they are linked form a cyclopropyl group.

11. A method according to claim 8, which comprises administering a member selected from the group consisting of
2- methyl-(3',4'-dichloro-2-fluoro-biphenyl-4-yl)propionic acid;
a pharmaceutically acceptable salt of 2- methyl-(3',4'-dichloro-2-fluoro-biphenyl-4-yl)propionic acid;

1-(3',4'-dichloro-2-fluorobiphenyl-4-yl)cyclopropanecarboxylic acid; and a pharmaceutically acceptable salt of 1-(3',4'-dichloro-2-fluorobiphenyl-4-yl)cyclopropanecarboxylic acid.

12. A method according to claim 11, which comprises administering 1-(3',4'-dichloro-2-fluorobiphenyl-4-yl)cyclopropanecarboxylic acid, a pharmaceutically acceptable salt thereof.

13. A method according to claim 1, wherein said disease is senile systemic amyloidosis.

14. A method according to claim 1, wherein said disease is familial amyloidosis polyneuropathy.

15. A method according to claim 14, wherein said familial amyloidosis polyneuropathy is characterized by V30M mutation.

16. A method according to claim 4, wherein said disease is senile systemic amyloidosis.

17. A method according to claim 4, wherein said disease is familial amyloidosis polyneuropathy.

18. A method according to claim 17, wherein said familial amyloidosis polyneuropathy is characterized by V30M mutation.

19. A method according to claim 4, wherein said disease is familial amyloidosis cardiomyopathy.

20. A method according to claim 19, wherein said familial amyloidosis cardiomyopathy is characterized by a V122I mutation.

21. A method according to claim 8, wherein said disease is senile systemic amyloidosis.

22. A method according to claim 8, wherein said disease is familial amyloidosis polyneuropathy.

23. A method according to claim 22, wherein said familial amyloidosis polyneuropathy is characterized by V30M mutation.

24. A method according to claim 8, wherein said disease is familial amyloidosis cardiomyopathy.

25. A method according to claim 24, wherein said familial amyloidosis cardiomyopathy is characterized by a V122I mutation.

* * * * *